(12) United States Patent
Shah et al.

(10) Patent No.: US 7,939,489 B2
(45) Date of Patent: May 10, 2011

(54) OIL ABSORBENT TOPICAL COMPOSITIONS AND METHODS FOR USING SAME

(75) Inventors: Arvind Shah, Suffern, NY (US); Gopinathan K. Menon, Wayne, NJ (US); Derrick B. McKie, Brooklyn, NY (US); Vincent T. Polywoda, Suffern, NY (US); Christos D. Kyrou, Goshen, NY (US); Michele C. Duggan, Middletown, NY (US)

(73) Assignee: Avon Products, Inc., New York, NY (US)

( * ) Notice: Subject to any disclaimer, the term of this patent is extended or adjusted under 35 U.S.C. 154(b) by 1199 days.

(21) Appl. No.: 10/328,204

(22) Filed: Dec. 23, 2002

(65) Prior Publication Data

US 2004/0120911 A1 Jun. 24, 2004

(51) Int. Cl.
*A61K 9/00* (2006.01)

(52) U.S. Cl. ......... 514/1; 424/400; 424/401; 424/78.08; 424/78.17

(58) Field of Classification Search ............ 424/78.03, 424/401, 61; 514/881, 871
See application file for complete search history.

(56) References Cited

U.S. PATENT DOCUMENTS

| | | | |
|---|---|---|---|
| 4,529,587 A * | 7/1985 | Green | 424/70.8 |
| 4,640,932 A | 2/1987 | Fong et al. | |
| 4,870,010 A * | 9/1989 | Hayes | 424/114 |
| 5,152,933 A * | 10/1992 | Holland | 510/340 |
| 5,558,872 A | 9/1996 | Jones et al. | |
| 5,614,178 A * | 3/1997 | Bloom et al. | 424/60 |
| 5,617,178 A * | 4/1997 | Goggins | 355/22 |
| 5,690,923 A | 11/1997 | DeVringer et al. | |
| 6,001,373 A * | 12/1999 | Igo-Kemenes et al. | 424/401 |
| 6,083,516 A * | 7/2000 | Curtis et al. | 424/401 |
| 6,267,951 B1 | 7/2001 | Shah et al. | 424/61 |
| 6,303,105 B1 | 10/2001 | Shah et al. | 424/61 |
| 2005/0004274 A1 * | 1/2005 | Healy et al. | 524/80 |
| 2005/0004374 A1 * | 1/2005 | Kim et al. | 549/200 |

FOREIGN PATENT DOCUMENTS

| | | | |
|---|---|---|---|
| WO | WO 95/09598 | | 4/1995 |
| WO | WO 96/03962 | | 2/1996 |
| WO | WO 96/03964 | | 2/1996 |
| WO | WO 96/15760 | | 5/1996 |
| WO | WO 00/07627 | | 2/2000 |
| WO | WO 00/18367 | | 4/2000 |
| WO | WO 00/49997 | | 8/2000 |
| WO | WO0004997 | * | 8/2000 |
| WO | WO0049997 | * | 8/2000 |
| WO | WO 00/73374 | | 12/2000 |
| WO | WO 03/090707 | | 11/2003 |

OTHER PUBLICATIONS

Sinerga Corporation, European Product Safety Sheet for Tiolisnia Complex 30, Dec. 10, 1993.*
Tiolisina Complex 30 product information sheet.*
Tiolisina Complex 30, Sinerga Corp, European Product Safety, Dec. 10, 1993.*
Sinerga, Tiolisina Complex 30 product information sheet.*
Tiolisina Complex 30, Sinerga Corp, European Product Safety Sheet.*
Arch Personal Care Products, Gel Base Product Information Sheet. Customer service was also contacted on Oct. 9, 2009 to inquire as to when the copolymer become commerically available. Kathy Defortunate indicated that it has been available at least since 1998.*
Brooks Industrys, Product Listing.*
Arch Personal Care Products, Gel Base Product Information Sheet.*
Brooks Industryes, product listing.*
Tiolsina Complex 30, Singerga Corp, European Product Safety Sheet.*
European Search Report dated Oct. 20, 2006.
International Search Report dated Nov. 2, 2004 from corresponding PCT Application No. PCT/US03/40552.
Tiolisina Complex-30 Water-Soluble Antiseborrheic, Sinerga Cosmetics Company, Edizione 1991.

* cited by examiner

*Primary Examiner* — Robert A Wax
*Assistant Examiner* — Melissa S Mercier
(74) *Attorney, Agent, or Firm* — Joan M. McGillycuddy; Charles J. Zeller

(57) ABSTRACT

There are provided topical compositions and methods for cleaning oil from the skin, nail or hair. The compositions have a vehicle and an effective amount of an oil-absorbing ingredient having an ethylene mixed block copolymer. There is also provided compositions and methods for treating acne, acne-related conditions, acne-prone skin and blemishes.

25 Claims, No Drawings

OIL ABSORBENT TOPICAL COMPOSITIONS AND METHODS FOR USING SAME

BACKGROUND OF THE INVENTION

1. Field of the Invention

The present invention relates to topical compositions and methods for absorbing oil from the skin, nail and hair. The present invention also relates to compositions and methods for treating acne.

2. Description of the Related Art

A common skin problem is the excess production and/or accumulation of oil in the skin. The excess production and/or accumulation may result in oily skin and can be a contributing factor in acnegenesis. Oily skin at the scalp may also render hair oily. Oily skin at the fingers and toes may also render the nails oily.

A multitude of compositions have been developed to address the problem of excess production and/or accumulation of oil in the skin. Alcohols have been used as drying agents. Substances employed include oil absorbers, oil dispersers, and sebum normalizers. Oil absorbers absorb or adsorb oil within their structure or matrix. Oil dispersers break up surface sebum and spread it over the surface of the skin to minimize oily appearance and feel on the skin. Sebum normalizers adjust sebum excretion to normal levels.

It would be desirable to have a topical composition that provides enhanced efficacy in reducing accumulation compared to known compositions. It would be further desirable to have a topical composition that provides enhanced efficacy in absorbing oil. It would be further still desirable to have a method for cleaning oil from the skin, nail and hair.

SUMMARY OF THE INVENTION

An object of the present invention is to provide topical compositions and methods for cleaning and/or absorbing oil from the skin, nail and hair. According to this object, the compositions have an effective amount of an oil-absorbing ingredient and a vehicle, and is applied to the skin, nail or hair. The oil-absorbing ingredient is an ethylene mixed block copolymer.

Another object of the present invention is to provide compositions and methods for treating acne, acne-prone skin, acne-related skin conditions and/or blemishes. The compositions have an effective amount of an oil-absorbing ingredient and a vehicle, which is applied to the skin. The oil-absorbing ingredient has an ethylene mixed block copolymer.

DETAILED DESCRIPTION OF THE INVENTION

It has been surprisingly found that there could be a topical composition that can provide enhanced cleaning and removal of oil from the skin, nail or hair. It has also been surprisingly found that there could be a topical composition that provides enhanced efficacy in treating acne, acne-prone skin, acne-related skin conditions and/or blemishes.

The present composition provides enhanced cleaning and removal of oil by the incorporation of an oil-absorbing agent or ingredient. The oil-absorbing ingredient absorbs and/or adsorbs oil within its structure or matrix.

The oil-absorbing ingredient is present in an amount effective to clean the skin, nail or hair. Typically, the oil-absorbing ingredient will be present at about 0.001 weight percent (wt %) to about 50 wt % based on the total weight of the composition. Preferably, the oil-absorbing ingredient will be present at about 0.01 wt % to about 5 wt % based on the total weight of the composition.

The oil-absorbing ingredient preferably takes the form of an ethylene mixed block copolymer (EMB copolymer). A preferred EMB copolymer is known by the INCI (International Cosmetic Ingredient) name of butylene/ethylene/propylene copolymer. Some literature indicates that there is a newly proposed INCI name for this copolymer, namely styrene/ethylene/propylene copolymer. As used herein, EMB copolymer shall include a copolymer of ethylene and propylene, together with butylene or styrene. The preferred copolymer is typically supplied commercially in the form of a substantially colorless, odorless gel. The solvent in the gel as commercially supplied is typically isododecane. Other useful solvents are hydrocarbons, including isoparaffin. The gel as commercially supplied is typically about 15 wt % copolymer and about 85 wt % isododecane. If desired, the solvent can function as a vehicle in the present composition. The preferred copolymer has the propylene monomeric content described above and preferably has substantially, and most preferably has entirely, that monomeric content. The preferred copolymer has a viscosity of 50,000 cps to 100,000 cps at 25° C. as measured on a Brookfield Viscometer on Spindle D. The preferred copolymer is sold as GEL BASE by Arch Personal Care Products.

The present compositions may optionally have one or more other oil-absorbing ingredients in addition to the EMB copolymer. Suitable additional oil-absorbing ingredients include, but are not limited to kaolin, cyclopentasiloxane, polydimethylsiloxane, silica shells, fumed silica, and styrene/rubber elastomers. Suitable styrene/rubber elastomers include styrene/rubber diblock and triblock copolymers. Such rubber block copolymers for use in the present invention include ethylene/propylene and ethylene/butylene combinations. Most preferred are the KRATON G block copolymers marketed by Kraton Polymers. The additional one or more oil-absorbing ingredients will typically be present at about 0.001 wt % to about 50 wt % based on the total weight of the composition. Preferably, the additional one or more oil-absorbing ingredients are present at about 0.01 wt % to about 5 wt % based on the total weight of the composition.

The present compositions may optionally also have one or more oil-dispersing agents or ingredients. Oil-dispersing ingredients break up surface sebum and spread it over the surface of the skin, hair or nails to minimize oily appearance and feel on the skin, hair or nails. They differ in action from oil-absorbing agents or ingredients in that they do not absorb/adsorb oil. Such suitable oil-dispersing ingredients include, but not limited to, rhamnolipid and sophorolipid biosurfactants (marketed by Jeneil Biosurfactant Co.) and polylipid protein sulfates. A most preferred oil-dispersing ingredient is sodium $C_8$-$C_{16}$ alkyl succinyl lactoglobulin sulfonate (BIOPOL OE marketed by Arch Personal Care Products). The oil-dispersing ingredient will typically be present at about 0.001 wt % to about 10 wt % based on the total weight of the composition. Preferably, the oil-dispersing ingredient is present at about 0.01 wt % to about 5 wt % based on the total weight of the composition.

The present compositions may optionally also have one or more sebum-normalizing agents or ingredients. A sebum normalizer adjusts sebum excretion to normal levels. Such sebum-normalizing ingredients suitable for use in the present compositions include, but are not limited to, farnesyl acetate and lysine carboxymethyl cysteinate/lysine thiazolidine carboxylate (TIOLISINA COMPLEX-30 marketed by Sinerga Cosmetics Co.). A most preferred sebum-normalizing ingredient is lysine carboxymethyl cysteinate/lysine thiazolidine carboxylate. The one or more sebum-normalizing ingredients will typically be present at about 0.001 wt % to about 5 wt % based on the total weight of the composition. Preferably, the sebum-normalizing ingredients are present at about 0.01 wt % to about 1 wt % based on the total weight of the composition.

In a preferred embodiment, the present composition has an oil-dispersing ingredient and a sebum-normalizing ingredient in addition to the oil-absorbing ingredient (EMB copolymer). The preferred composition affords three different modes of action, oil absorption, oil dispersion and sebum normalization, in cleaning oil from the skin, nail or hair, as well as treating acne and acne-related skin conditions.

The present composition may optionally have a keratolytic agent or ingredient to assist in the treatment of acne. Such keratolytic ingredients include, but are not limited to, salicylic acid, glycolic acid, chlorosalicylic acid, oxa acid, and oxa diacid. A preferred keratolytic ingredient is salicylic acid. Preferably, the salicylic acid is present at about 0.5 wt % to about 2.0 wt % based on the total weight of the composition. Preferably, the salicylic acid is provided in the form of liposomes with soya lecithin in aqueous butylene glycol.

The present composition may take any product form known in the art. Such forms include aerosol, cream, lotion, gel, dispersion, emulsion, foam, solution, suspension, ointment, mask, mousse, patch, powder, pump spray, stick, tape, towelette, cream-to-powder, wet/dry pressed powder, loose powder and pomade (anhydrous or hydrous).

A preferred embodiment of the composition takes the form of an emulsion. Useful emulsion forms include oil-in-water, water-in-oil, silicone-in-water, water-in-silicone and triple emulsions.

The present composition may take a variety of end-product forms such as a sunscreen composition, a body wash, a hand wash, a facial cleaner or cleanser, an anti-acne composition, a conditioning composition, a shampoo, and a hair conditioner.

The present composition may also take the form of a make-up composition. Such make-up compositions include blush, bronzer, mascara, foundation, lipstick, oil, rouge, concealer, shine stopper primer, and powder.

The present compositions will be topically applied and employed in different ways depending upon the product and the end use application. In application to the skin, such as face, back, forehead, hand, foot and body, the product will typically be rubbed or dabbed on. In application to the hair, the product will typically be dabbed on and worked in with the hands or a brush or other applicator. After application, the product in some instances may be washed off, wiped away or otherwise removed relatively quickly. In other instances, the product may be left for a period of time, e.g. overnight or all day, and then removed. In still other instances, the product may be left to wear off. Products like cleansers, washes and shampoos are removed relatively soon after application, while cosmetics and sunscreen compositions are typically removed after an extended period of time, such as all day.

Compositions useful in the present method have a vehicle that is pharmaceutically or cosmetically acceptable. Such vehicles include, but are not limited to, one or more $C_{1-4}$ alcohols, fatty alcohols, fatty ethers, fatty esters, isododecane, polyols, glycols, liposomes, laminar lipid materials, water, or any combinations thereof.

The compositions of the present invention may also include one or more aqueous gelling agents, such as hydroxyethylcellulose, xanthan gum, polyacrylamide, and PVM/MA decadiene crosspolymer; neutralizing agents, such as sodium hydroxide, potassium hydroxide, ammonium hydroxide; and silicones, such as cyclomethicone, dimethicone, and phenyl trimethicone.

Optionally, compositions useful in the present method can include one or more of the following additional ingredients: amino acids, anesthetics, anti-acne agents, anti-allergenics, antifungals, antimicrobials, anti-inflammatory agents, anti-irritants, antineoplastics, antioxidants, antiseptics, antivirals, chelating agents, colorants, depigmenting agents, emollients, emulsifiers, exfolients, film formers, fragrances, humectants, hypopigmenting agents, immune system boosting agents, immune system suppressing agents, insect repellents, lubricants, moisturizers, pharmaceutical agents, photostabilizing agents, preservatives, retinoids, skin protectants, skin penetration enhancers, staining agents, sunscreens, stabilizers, surfactants, thickeners, viscosity and/or rheology modifiers, vitamins, or any combinations thereof.

The following Examples 1 and 2 are representative formulas of a sebum control gel primer make-up product and an anti-acne product, respectively. Unless otherwise indicated, all percentages or parts are by weight.

EXAMPLE 1

| Ingredient | Wt. % |
|---|---|
| Isododecane/ethylene Mixed Block Copolymer | 60 |
| Isododecane | 29.2 |
| Methylparaben | 0.3 |
| Laurylmethicone copolyol | 3 |
| Polyglycerol diisostearate | 4.5 |
| Glyceryl tribehenate | 2 |
| Titanium dioxide | 1 |

EXAMPLE 2

| Ingredient | Wt. % |
|---|---|
| Oil-absorbing agent (e.g., kaolin, silica, isododecane/ethylene mixed block copolymer) | 0.001 to 5 |
| Oil-dispersing agent (e.g., sodium $C_8$-$C_{16}$ isoalkylsuccinyl lactoglobulin sulfonate) | 0.001 to 1 |
| Sebum-normalizing agent (e.g. farnesyl acetate, lysine carboxymethyl cysteinate) | 0.001 to 0.5 |
| Aqueous Gelling agent (e.g. hydroxyethylcellulose, xanthan gum, polyacrylamide, PVM/MA decadiene crosspolymer) | 0.5 to 2 |
| Humectants (e.g., glycerin, propylene glycol, butylene glycol) | 0.5 to 5 |
| Emulsifiers (e.g., steareth-2, steareth-21, peg-40 stearate, polyglycerol diisostearate) | 0.5 to 2 |
| Keratolytic agents (e.g., salicylic acid, glycolic acid, oxa acid, oxa diacid) | 0.5 to 8 |
| Neutralizing agents (e.g., sodium hydroxide, potassium hydroxide, ammonium hydroxide) | 1.5 to 3 |
| Emollients (e.g., $C_{12-15}$ alkyl benzoate, cocoglycerides, hydrogenated polyisobutane) | 0.5 to 5 |
| Viscosity modifying agents (e.g., cetyl alcohol, behenyl alcohol, | 0.5 to 5 |

-continued

| Ingredient | Wt. % |
|---|---|
| stearyl alcohol, glyceryl tribehenate) | |
| Silicones | 1 to 6 |
| (e.g., cyclomethicone, dimethicone, phenyl trimethicone, lauryl methicone copolyol) | |
| Preservatives | 0.5 to 1.5 |
| (e.g., methylparaben, propylparaben, benzyl alcohol, phenoxyethanol) | |
| Fragrance | 0.1 to 0.5 |
| Water | QS |

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A method for cleaning oil from the skin comprising washing or cleaning the skin of the face with a composition comprising: (i) a cosmetically acceptable vehicle; (ii) an effective amount of an oil-absorbing ingredient, wherein said absorbing ingredient is an ethylene mixed block copolymer (EMB copolymer) of ethylene, propylene, and butylene having the INCI (International Cosmetic Ingredient) name butylene/ethylene/propylene copolymer; (iii) an oil dispersing ingredient comprising a member of the group consisting of a biosurfactant, polylipid protein sulfates, and sodium $C_8$-$C_{16}$ alkyl succinyl lactoglubulin sulfonate; and (iv) a sebum normalizing ingredient, wherein said sebum normalizing agent is lysine carboxymethyl cysteinate/lysine thiazolidine carboxylate.

2. The method of claim 1; wherein the oil-dispersing ingredient is a biosurfactant.

3. The method of claim 1, wherein the copolymer is present at about 0.001 wt % to about 50 wt % based on the total weight of the composition.

4. The method of claim 1, wherein the copolymer is present at about 0.01 wt % to about 5 wt % based on the total weight of the composition.

5. The method of claim 2, wherein said biosurfactant is selected from the group consisting of a rhamnolipid biosurfactant and a sophorolipid biosurfactant.

6. The method of claim 1, wherein the oil-dispersing ingredient is present at about 0.01 wt % to about 5 wt % based on the total weight of the composition.

7. The method of claim 1, wherein the oil-dispersing ingredient is sodium $C_8$-$C_{16}$ succinyl lactoglobulin sulfonate.

8. The method of claim 1, wherein the sebum-normalizing ingredient is present at about 0.001 wt % to about 5 wt % based on the total weight of the composition.

9. The method of claim 1, wherein the copolymer has a viscosity of 50,000 cps to 100,000 cps at 25° C.

10. A method for cleaning oil from the skin comprising washing or cleaning the skin of the face with a composition comprising: (i) a cosmetically acceptable vehicle; (ii) an oil-absorbing effective amount of an ethylene mixed block copolymer (EMB copolymer) of ethylene, propylene, and butylene having the INCI (International Cosmetic Ingredient) name butylene/ethylene/propylene copolymer; (iii) a material selected from the group consisting of kaolin, cyclopentasiloxane, polydimethylsiloxane, silica and styrene/rubber elastomers; (iv) an oil-dispersing ingredient, selected from the group consisting of a biosurfactant, polylipid protein sulfates, and sodium $C_8$-$C_{16}$ alkyl succinyl lactoglobulin sulfonate; and (v) a sebum normalizing agent, wherein the sebum-normalizing ingredient is lysine carboxymethyl cysteinate/lysine thiazolidine carboxylate.

11. The method of claim 10, wherein the oil-dispersing ingredient is a biosurfactant.

12. The method of claim 11, wherein the biosurfactant is a rhamnolipid biosurfactant or a sophorolipid biosurfactant.

13. The method of claim 10, wherein the oil-dispersing ingredient is sodium $C_8$-$C_{16}$ alkyl succinyl lactoglobulin sulfonate.

14. The method of claim 10, wherein the oil-dispersing ingredient is a polylipid protein sulfate.

15. The method of claim 10, wherein the oil-dispersing ingredient is present at about 0.01 wt % to about 5 wt % based on the total weight of the composition.

16. The method of claim 10, wherein the oil-dispersing ingredient is sodium. $C_8$-$C_{16}$ alkyl succinyl lactoglobulin sulfonate.

17. The method of claim 10, wherein said sebum-normalizing ingredient is present at about 0.001 wt % to about 5 wt % based on the total weight of the composition.

18. The method of claim 17, wherein the sebum-normalizing ingredient is present at about 0.01 wt % to about 1 wt % based on the total weight of the composition.

19. The method of claim 10, wherein said composition further comprises a keratolytic agent.

20. The method of claim 19, wherein the keratolytic agent is a salicylic acid.

21. The method of claim 10, wherein the copolymer has a viscosity a 50,000 cps to 100,000 cps at 25° C.

22. The method of claim 10, wherein said vehicle comprises a member of the group consisting of $C_{1-4}$ alcohols, fatty alcohols, fatty-ethers, fatty esters, isododecane, polyols, glycols, liposomes. laminar lipid materials, water, or any combination thereof.

23. The method of claim 10, wherein the said vehicle comprises isodocecane.

24. The method of claim 10, wherein said composition comprises silica.

25. A method for treating acne comprising applying to acne-impacted skin a composition comprising: (i) a cosmetically acceptable vehicle; (ii) an oil-absorbing effective amount of an ethylene mixed block copolymer (EMB copolymer) of ethylene, propylene, and butylene having the INCE (International Cosmetic Ingredient) name butylene/ethylene/propylene copolymer; (iii) sodium $C_8$-$C_{16}$ alkyl succinyl lactoglobulin sulfonate; and (iv) a sebum normalizing agent, wherein the sebum-normalizing ingredient is lysine carboxymethyl cysteinate/lysine thiazolidine carboxylate.

* * * * *